US00PP10471P

United States Patent [19]

Lemon

[11] Patent Number: Plant 10,471

[45] Date of Patent: Jun. 30, 1998

[54] VARIETY OF GERANIUM PLANT NAMED 'PATRIOT SALMON BLUSH'

[75] Inventor: David Lemon, Lompoc, Calif.

[73] Assignee: John Bodger & Sons Company, So. El Monte, Calif.

[21] Appl. No.: 724,676

[22] Filed: Oct. 1, 1996

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 5,315 10/1984 Hofmann ..... Plt./87.12

P.P. 8,089 1/1993 Craig ..... Plt./87.12

*Primary Examiner*—Howard J. Locker

*Attorney, Agent, or Firm*—Fulwider Patton Lee Utecht, LLP

[57] ABSTRACT

The cultivar is characterized by the blushed salmon-pink bloom over medium green zoned foliage. Its quick rooting time and continuous flowering provides for superb cuttings and for quick recovery of the bloom following wet weather conditions. The cultivar performs extremely well outdoors, and an abundant amount of cuttings may be obtained from a single plant.

2 Drawing Sheets

BACKGROUND OF THE NEW PLANT

The present invention comprises a new and distinct cultivar of *Pelargonium×hortorum* known by the varietal name Patriot Salmon Blush (Oglevee No. 3087, Bodger No. 2GM 247-8). The new variety was discovered in a selective breeding program by David Lemon at Bodger Seeds, Ltd., Lompoc, Calif. The new variety is a selection from the crossing of Jubilee (U.S. Plant Pat. No. 8,089) which has a watermelon colored flower, with Bodger No. 1 GM 89-1 (unpatented) which is a salmon colored seedling, as distinguished from the claimed cultivar which has a variegated salmon pink flower and medium green foliage.

The new cultivar was first asexually reproduced by cuttings at Oglevee Ltd., Connellsville, Pa., and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa., using full light, 60° Fahrenheit night temperature, 68° Fahrenheit day temperature, 72° Fahrenheit vent temperature and grown in a soilless media of constant fertilizer 200–250 parts per million of nitrogen and potassium has a response time of six weeks from the rooted cutting to a flowering plant in a 10.0 cm pot.

DESCRIPTION OF THE DRAWINGS

The accompanying drawings illustrate the new cultivar, the colors depicted being as nearly true as possible with color illustrations of this type.

Sheet 1 represents a side view of the new cultivar.

Sheet 2 is a top view.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings believed to have been potted on approximately Feb. 1, 1996 and flowering on approximately Mar. 14, 1996 under full light and greenhouse, and colorings were taken indoors under 200–200 foot candles of fluorescent cool white light using The R.H.S. Colour Chart of The Royal Horticultural Society of London.

The Plant

Classification:
- *Botanical.*—*Pelargonium×hortorum.*
- *Commercial.*—*Zonal florist's geranium Patriot Salmon Blush (Florist's geraniums are a high quality plant which also grows well outdoors).*

Form: Uniform, medium mound habit.
- *Height.*—19.0–24.0 cm above media surfaces.
- *Growth.*—Free basal branching.
- *Strength.*—No artificial support needed.

Foliage: Stalked leaf attachment; zone present.

Leaves:
- *Size.*—8.5–10.0 cm across.
- *Shape.*—Reniform; cordate base.
- *Margin.*—Crenate.
- *Texture.*—Pubescent; slightly reflective.
- *Color.*—Top: 137 C Green Group. Bottom: 139C Green Group. Zone: 147 A Yellow-Green Group.
- *Ribs and veins.*—Palmate venation: Color: 145 B Yellow-Green Group.

Petioles:
- *Length.*—5.5–800 cm.
- *Color.*—144 A Yellow-Green Group.

Stem:
- *Color.*—144 B Yellow-Green Group.
- *Internodes.*—3.0 cm–4.5 cm.

The Bud (Umbel)

Shape: Upright, hemispherical cluster.

Size: 2.0 cm–5.0 cm.

Inflorescence

Blooming habit: Semi-double (any floret with 6 or more petals which still have anthers and filaments); free and early flowering, continuous.

Borne: Umbel; florets on pedicel, pedicel on peduncle; 5.0–9.0 cm above foliage.

Closed florets:
*Bud size.*—1.0–1.6 cm in length; 0.5–0.8 cm in width.
Size: Fully open bloom.—10.0 cm, 12.0 cm across.
Open florets:
*Form.*—Flat to slightly cupped; 24 florets per inflorescence appearing which can increase to an average of 54 florets per inflorescence on older plants.
*Color.*—Old bloom: Top: Base/tip — Red Group 52C. Middle petal Red Group 41C. Light streaks Red Group 49C. Dark streaks Red Group 53D. Bottom: Tip 52C Red Group. Base Red Group 49D. Young bloom: Main petal color 38A red group. Base 155D White Group. Light streaks 38D Red Group. Tip of petal 52C Red Group. Bottom: Main color 49B Red Group. Base color 49D Red Group. Dark streaks 43D Red Group.
*Petals.*—5–8.
*Size.*—4–5 cm.
*Texture.*—Smooth, appearance from a distance is a blushed salmon-pink above medium green zoned foliage.
Petaloids:
*Quantity.*—0–2.
*Shape.*—Curled.
*Color.*—Top: 52C Red Group. Bottom: 49D Red Group.
Pedicel:
*Length.*—2.5–3 cm.
*Color.*—Yellow-Green Group 146D at base — 53A Red Group at tip.
Peduncle:
*Length.*—15.0–18.0 cm.
*Color.*—146 D Yellow-Green Group.
Persistence:
*Disease resistance.*—Not known.
*Lasting quality.*—Unknown.

Reproductive Organs

Stamens:
*Anthers.*—Length: 7–9 mm.
*Filaments,*—Length: 6–8 mm. Color: 155D White Group.
*Pollen.*—171 B Greyed Orange Group.
Pistils:
*Number.*—1.
*Length.*—7–8 mm.
*Stigma.*13 Color: 53A Red Group; 5–6 parted.
*Style.*—Length: 2 mm.
Ovaries:
*Color.*—143D Yellow-Green Group; Pubescent; Superior.
*Length.*—3–4 mm.
Fruit: None.

General Characteristics

Patriot Salmon Blush is an improvement over the current variety "Palais" (U.S. Plant Pat. No. 5,315) which is a double flowered geranium having salmon pink flowers with light margins and a medium dark green foliage, the claimed cultivar is a semi-doubled flower having a more evenly distributed coloration and medium green foliage, both in cutting production and outdoor performance. Patriot Salmon Blush withstands very high temperatures outdoors and rebounds quickly. The distinct zone and the blushed salmon—pink flower are very pleasing to the eye.

I claim:

1. A new and distinct variety of geranium plant, substantially as shown and described.

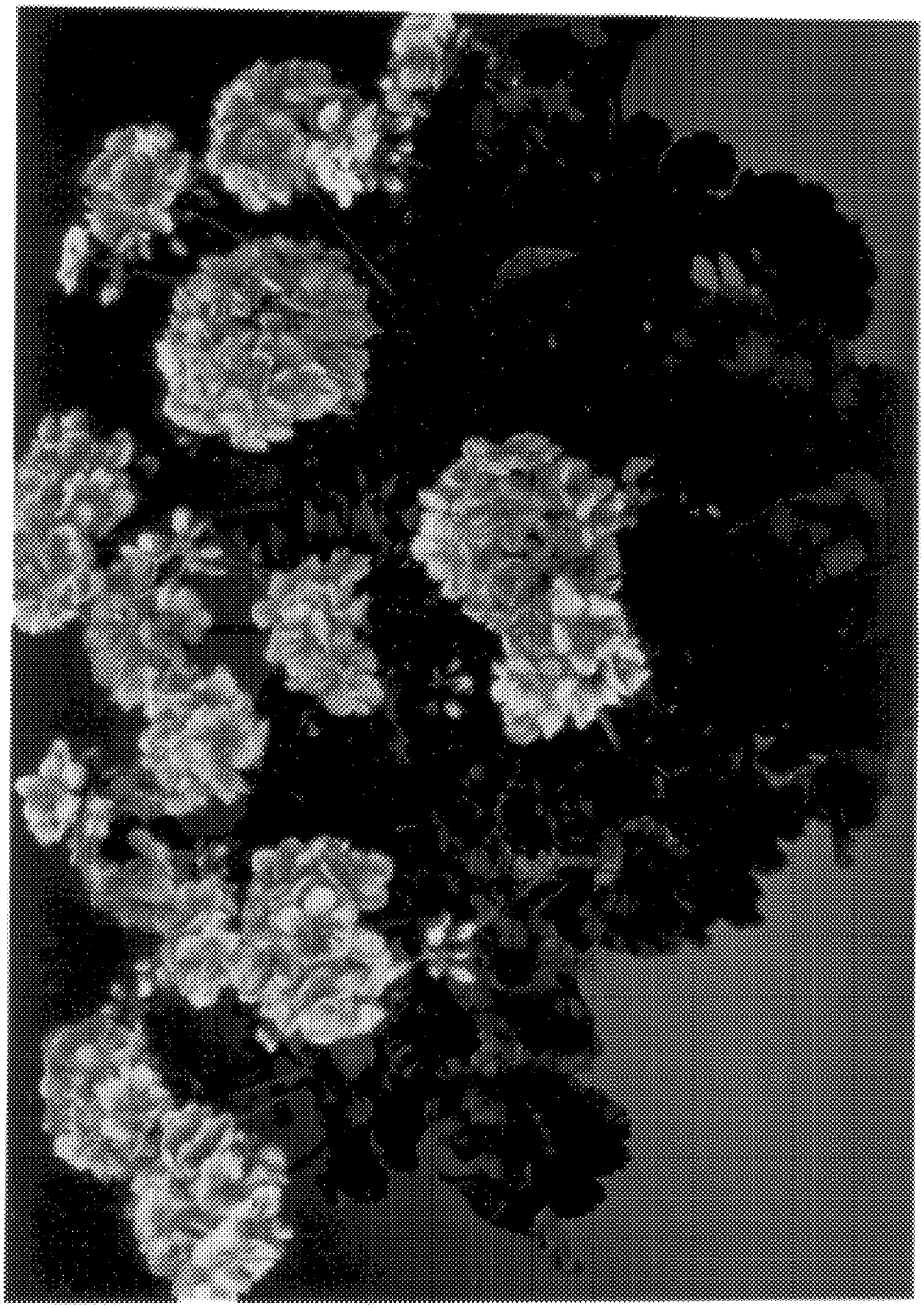

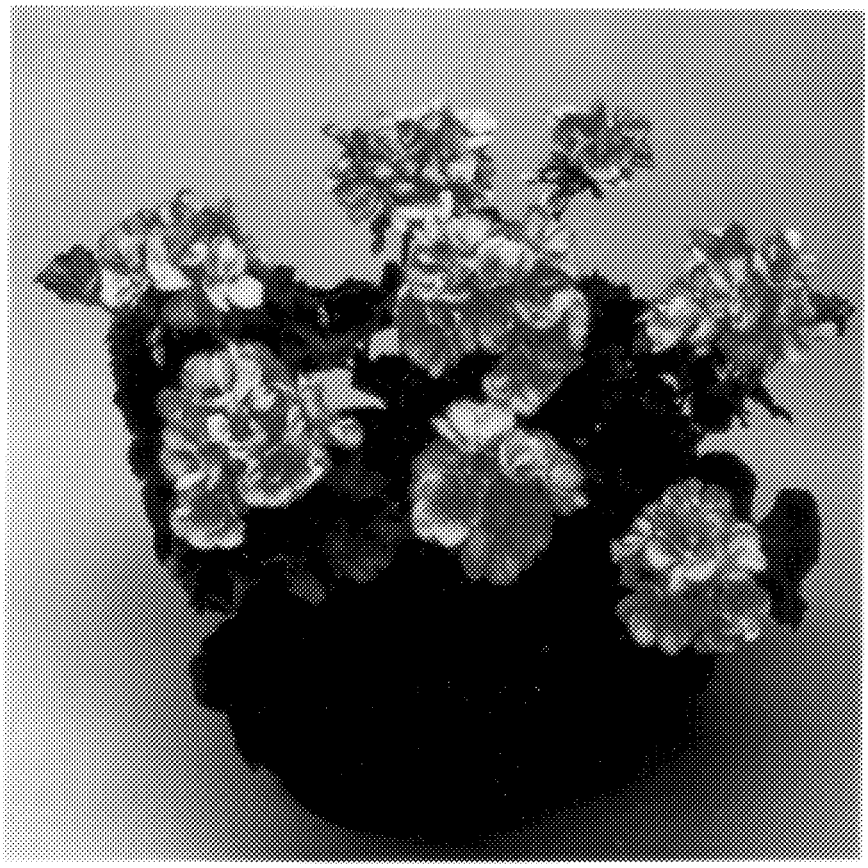

* * * * *